(12) United States Patent
Johnson

(10) Patent No.: US 8,642,655 B2
(45) Date of Patent: Feb. 4, 2014

(54) SYSTEMS AND METHODS FOR PREVENTING CANCER AND TREATING SKIN LESIONS

(76) Inventor: Benjamin Johnson, Evergreen, CO (US)

( * ) Notice: Subject to any disclaimer, the term of this patent is extended or adjusted under 35 U.S.C. 154(b) by 0 days.

(21) Appl. No.: 13/044,532

(22) Filed: Mar. 9, 2011

(65) Prior Publication Data

US 2012/0232148 A1   Sep. 13, 2012

(51) Int. Cl.
*A61K 31/185* (2006.01)

(52) U.S. Cl.
USPC ............................................. 514/561

(58) Field of Classification Search
USPC ........................................... 514/561
See application file for complete search history.

(56) References Cited

U.S. PATENT DOCUMENTS

| | | |
|---|---|---|
| 2,460,707 A | 2/1949 | Moray |
| 3,105,792 A | 10/1963 | White |
| 3,325,357 A | 6/1967 | Irani |
| 3,480,185 A | 11/1969 | Steinberg et al. |
| 3,876,373 A | 4/1975 | Glyptis |
| 3,937,810 A | 2/1976 | Mathur |
| 4,524,079 A | 6/1985 | Hofmann |
| 4,784,849 A | 11/1988 | Tutsky |
| 5,034,228 A | 7/1991 | Meybeck et al. |
| 5,074,035 A | 12/1991 | Tyznik |
| 5,091,142 A | 2/1992 | Petit |
| 5,552,274 A | 9/1996 | Oyama et al. |
| 5,658,322 A | 8/1997 | Fleming |
| 5,709,849 A | 1/1998 | Ito et al. |
| 5,853,755 A | 12/1998 | Foldvari |
| 5,908,444 A | 6/1999 | Azure |
| 5,952,312 A | 9/1999 | Birkmayer |
| 5,981,182 A | 11/1999 | Jacobson |
| 6,004,257 A | 12/1999 | Jacobson |
| 6,060,293 A | 5/2000 | Bohr et al. |
| 6,217,604 B1 | 4/2001 | Azure et al. |
| 6,312,703 B1 | 11/2001 | Orthoefer |
| 6,391,863 B1 | 5/2002 | Philippe et al. |
| 6,596,305 B1 | 7/2003 | Edgerly-Plug |
| 6,764,693 B1 | 7/2004 | Smith |
| 6,974,561 B1 | 12/2005 | Thomason |
| 7,011,845 B2 | 3/2006 | Kozbor et al. |
| 7,160,726 B2 | 1/2007 | Mansbridge |
| 7,280,874 B2 | 10/2007 | Boehm |
| 7,306,725 B2 | 12/2007 | Bartl et al. |
| 7,347,944 B2 | 3/2008 | Bagley |
| 7,777,074 B2 * | 8/2010 | Kramer et al. ............... 562/512 |
| 7,799,782 B2 * | 9/2010 | Munson et al. ........... 514/234.5 |
| 2003/0118616 A1 | 6/2003 | Lee et al. |
| 2003/0134781 A1 | 7/2003 | Carmichael et al. |
| 2003/0232091 A1 | 12/2003 | Shefer et al. |
| 2004/0247619 A1 | 12/2004 | Hambrook |
| 2005/0123499 A1 | 6/2005 | Majumdar |
| 2006/0081542 A1 | 4/2006 | Pulis et al. |
| 2006/0216251 A1 | 9/2006 | Morariu |
| 2007/0157791 A1 | 7/2007 | Mazursky |
| 2007/0243158 A1 | 10/2007 | Ronfard et al. |
| 2007/0292400 A1 | 12/2007 | Lipton et al. |
| 2008/0219917 A1 | 9/2008 | Koruga |
| 2008/0234194 A1 | 9/2008 | Brem et al. |

FOREIGN PATENT DOCUMENTS

| | | | |
|---|---|---|---|
| DE | 19533330 | * | 3/1997 |
| WO | 96/31194 | | 10/1996 |

OTHER PUBLICATIONS

Sauermann's CAS: 126: 203744, 1997.*
Egbaria, et al., "Liposomes as a Topical Drug Delivery System", Advanced Drug Delivery Reviews, 5 pp., 287-300, 1990.
Kim, "Tyrosinease Inhibitors from Natural and Synthetic Sources, Structure, Inhibition Mechanisms and Perspective for the Future", Cellular and Molecular Life Sciences, vol. 62, pp. 1707-1723, 2005.
The Merck Index, 1983, pp. 5271.

* cited by examiner

*Primary Examiner* — Rei-tsang Shiao
(74) *Attorney, Agent, or Firm* — Mark D. Trenner; Trenner Law Firm

(57) ABSTRACT

Systems and methods of using a composition containing at least one or more amino acids for topical application to skin to prevent cancer and treat skin lesions.

3 Claims, No Drawings

SYSTEMS AND METHODS FOR PREVENTING CANCER AND TREATING SKIN LESIONS

FIELD OF THE INVENTION

This invention relates to the field of preventing cancer and treatments for skin lesions.

BACKGROUND OF THE INVENTION

Skin cancer occurs when errors (mutations) form the in the DNA of healthy skin cells. The mutations cause the cells to grow out of control and form a mass of cancer cells. Skin cancer begins in your skin's top layer—the epidermis. The epidermis is a thin layer that provides a protective cover of skin cells that your body continually sheds. The epidermis contains three main types of cells:
  Squamous cells lie just below the outer surface and function as the skin's inner lining.
  Basal cells, which produce new skin cells, sit beneath the squamous cells.
  Melanocytes—which produce melanin, the pigment that gives skin its normal color—are located in the lower part of your epidermis. Melanocytes produce more melanin when you're in the sun to help protect the deeper layers of your skin. Extra melanin produces the darker color of tanned skin.

SUMMARY OF THE INVENTION

The present invention provides systems and method for preventing skin cancer and treatment of skin lesions. In a preferred embodiment, the present invention uses combinations of amino acids in a topical application for repairing the skin damage that results in skin cancer or lesions. Amino acids are critical to the health of the skin. They are the building blocks of many proteins, enzymes, antioxidants as well as being the material from which DNA and Collagen are constructed and repaired.

DETAILED DESCRIPTION OF PREFERRED EMBODIMENTS

The present invention, in a descriptive embodiment, provides a topical application treating and preventing skin cancer and lesions. This topical application, in a preferred embodiment, includes the following formulations. It is to be expressly understood that this embodiment is intended for descriptive purposes only and other variations and alternative embodiments are within the scope of the invention.

The topical application includes the use of individual amino acids, either on their own or in groups of two or more, at a range of percentages in formulation between 0.1%-50%. These amino acids, either individually or in combinations of groups of two or more include but are not limited to; alanine, asparagine, aspartic acid, arginine, cysteine, cystine, glutamine, glycine, glutamic acid, histidine, lysine, leucine, phenylalanine, methionine, serine, proline, tryptophan, threonine, tyrosine, valine, taurine, guanidine, carnitine, adenine, guanine, thymine, cytosine, uracil, citruline, GABA, ornithine, glutamic acid, in their original chemical state and/or with modifications (example; histidine monochloride monohydrate).

These amino acids may be liposomally delivered or not. They may also be added separately to other products as a powder or combined into a serum and/or emulsion.

Liposomes

Liposomes are microscopic spheres made from fatty materials, predominantly phospholipids. Because of their similarity to phospholipid domains of cell membranes and an ability to carry substances, liposomes can be used to protect active ingredients and to provide time-release properties in medical treatment.

Liposomes are made of molecules with hydrophilic and hydrophobic ends that form hollow spheres. They can encapsulate water-soluble ingredients in their inner water space, and oil-soluble ingredients in their phospholipid membranes. Liposomes are made up of one or more concentric lipid bilayers, and range in size from 50 nanometers to several micrometers in diameter. Liposomal formulations have been used for many years to enhance the penetration of topically applied ingredients. Liposomes are made from lecithin, egg or it can be synthesized. These phospholipids can be both hydrogenated and non-hydrogenated. Phosphatidylcholine is extracted from these sources and can be both saturated and unsaturated. Other phospholipids including essential fats like linoleic acid and alpha linolenic acid can be used. Additionally, polyethylene glycol and cholesterol are considered liposomal material because of their lipid structure.

Preparation of Exemplary Therapeutic Compositions

Accordingly, a preferred embodiment of the present invention provides cosmetic as well as therapeutic compositions containing amino acids coated in liposomal material which when topically administered will increase the proliferation, growth, division and differentiation of cells. These cells are then able to improve skin health as well as to treat skin wounds and infections.

The amino acids of the instant invention may be formulated for topical application in aqueous or non-aqueous solution, gel, lotion, cream or ointment containing 0.1 to 20 percent and preferably from 0.5 to 15 percent by weight of the total composition. Other additives may be used to stabilize or otherwise provide functionality such as solvents, plasticizers, emulsify, stiffen, or other functions. Liposomal lecithin or a liposome substitute or other lipid preparations are added to the above solution with mixing until a uniform consistency is obtained.

To prepare a typical aqueous solution, the amino acids are dissolved in a mixture of water, ethanol and propylene glycol in a volume ratio of 30:50:20, respectively. Sodium metabisulfite is then added to the above solution. Liposomes such as lecithin or phosphatidylcholine or other lipid preparations are added to the above solution with mixing until a uniform consistency is obtained.

To prepare a typical non-aqueous solution, the amino acids are dissolved in a mixture of ethanol, isopropyl myristate and squalane in a volume ratio of 70:20:10, respectively. BHT is then added to the above solution. Liposomes or liposome substitutes are added to this solution with mixing until a uniform consistency is achieved. When a combination composition is desired retinyl palmitate and/or hydroquinone, for example is added to the above non-aqueous solution. The preferred concentration of retinyl palmitate ranges from 1 to 5%. The concentration of hydroquinone may range from 1 to 5%, but the preferred concentration is 2% by weight of the total composition.

A typical cream or lotion containing amino acids is created by dissolving amino acids in ethanol, acetone, propylene glycol or other solvent. The solution thus prepared is then admixed with commonly available oil-in-water emulsions. BHT or sodium metabisulfite may be added to such emulsions to stabilize the amino acids. Liposomes or liposome substitutes are added to this solution with mixing until a uniform consistency is achieved.

A typical gel composition is formulated by first dissolving amino acids in a mixture of ethanol, water and propylene glycol in a volume ratio of 50:30:20, respectively. A gelling agent such as hydroxyethylcellulose, hydroxypropylcellulose or hydroxypropylmethylcellulose is then added to the mixture with mixing. The preferred concentration of the gelling agent may range from 0.2 to 2 percent by weight of the total composition. Liposomes or liposome substitutes are added to this solution with mixing until a uniform consistency is achieved.

The above examples of formulations and compositions of descriptive embodiments are provided as a general explanation of the present invention. It is expressly noted that these examples are intended to be illustrative and not limiting.

Therapeutic Uses

The present invention may in various embodiments be used to increase the efficacy of the use of amino acids for therapeutically and cosmetically treating many skin disorders and in particular skin cancer and or lesions.

A preferred embodiment of the present invention increases the efficacy of a topical skin care product by increasing the penetration of amino acids that have been derived from stem cells or fibroblasts into the skin. Compositions containing amino acids are coated or mixed with liposomal materials as described above. The liposomal amino acids compound has been shown to increase the penetration of the amino acids thereby increasing the efficacy of the amino acids product.

The invention may be embodied in other specific forms without departing from the spirit or essential characteristics thereof. The present embodiments are therefore to be considered in all respects as illustrative and not restrictive, the scope of the invention being indicated by the appended claims and all changes which come within the meaning and equivalency of the claims are therefore intended to be embraced therein.

The above described formulations may be used with other known ingredients and combinations of ingredients to form a topical application that suitable for application onto the skin of humans and to provide additional benefits as is within the realm and knowledge of one skilled in the preparation of topical compositions.

The above formulations are provided for topical application in a product that helps prevent skin cancer and treat skin lesions.

What is claimed is:

1. A topical composition comprising: at least 1% of an amino acid including cysteine.

2. A topical composition comprising at least 1% of an amino acid proline.

3. A topical composition comprising at least 1% of amino acids lysine and glycine.

* * * * *